(12) United States Patent
Anderson et al.

(10) Patent No.: US 9,339,529 B2
(45) Date of Patent: May 17, 2016

(54) GLUCOSE-RESPONSIVE MICROGELS FOR CLOSED LOOP INSULIN DELIVERY

(71) Applicants: Massachusetts Institute of Technology, Cambridge, MA (US); The Children's Medical Center Corporation, Boston, MA (US)

(72) Inventors: Daniel G. Anderson, Sudbury, MA (US); Zhen Gu, Cambridge, MA (US); Robert S. Langer, Newton, MA (US)

(73) Assignees: Massachusetts Institute of Technology, Cambridge, MA (US); The Children's Medical Center Corporation, Boston, MA (US)

( * ) Notice: Subject to any disclaimer, the term of this patent is extended or adjusted under 35 U.S.C. 154(b) by 0 days.

(21) Appl. No.: 14/379,481

(22) PCT Filed: Feb. 19, 2013

(86) PCT No.: PCT/US2013/026633
§ 371 (c)(1),
(2) Date: Aug. 18, 2014

(87) PCT Pub. No.: WO2013/123492
PCT Pub. Date: Aug. 22, 2013

(65) Prior Publication Data
US 2015/0030641 A1    Jan. 29, 2015

Related U.S. Application Data

(60) Provisional application No. 61/600,394, filed on Feb. 17, 2012.

(51) Int. Cl.
| | | |
|---|---|---|
| A61K 9/00 | (2006.01) | |
| A61K 38/28 | (2006.01) | |
| A61K 38/44 | (2006.01) | |
| A61K 9/50 | (2006.01) | |
| A61K 9/51 | (2006.01) | |

(52) U.S. Cl.
CPC ........... *A61K 38/28* (2013.01); *A61K 9/0019* (2013.01); *A61K 9/5026* (2013.01); *A61K 9/5031* (2013.01); *A61K 9/5036* (2013.01); *A61K 9/5138* (2013.01); *A61K 9/5161* (2013.01); *A61K 38/44* (2013.01); *A61K 38/443* (2013.01); *C12Y 101/03004* (2013.01); *C12Y 111/01006* (2013.01)

(58) Field of Classification Search
None
See application file for complete search history.

(56) References Cited

U.S. PATENT DOCUMENTS

| 4,364,385 A | 12/1982 | Lossef | |
|---|---|---|---|
| 2008/0102114 A1* | 5/2008 | Koritala | A61K 9/1652 424/456 |

FOREIGN PATENT DOCUMENTS

WO    2006088473    8/2006

OTHER PUBLICATIONS

Anonymous, "Microgel—Devinition from Wiktionary, the free dictionary", URL:http//en.wiktionary.org/w/index.php?title=microogr1&printable=yes, retrieved Sep. 8, 2013.
Bartil, "Swelling behavior and release properties of pH-sensitive hydrogels based on methacrylic derivatives", Pharmaceutica,157(3):301-14 (2007).
Gu, et al, "Tailoring Nanocarriers for Intracellular Protein Delivery" Chemical Society Reviews, 40:3638-3655 (2011).
Kashyap, et al., "Design and evaluation of biodegradable, biosensitive in situ gelling system for pulsatile delivery of insulin" Biomaterials, 28(11):2051-60 (2007).
Kumareswaran, et al. "Artificial pancreas: an emerging approach to treat Type 1 diabetes" Expert Rev Med Devices, 6:401-10 (2009).
Pelton and Hoare, "Microgels and their synthesis: An introduction", Alberto Fernandez-Nievers (ed), Microgel Suspensions:Fundermentals and Applications,Wiley-WCH Verlag GmbH, Weinhelm, 3-32 (2011).
Podual, et al., "Dynamic behavior of glucose oxidase-containing microparticles of poly9ethyleme glycol)-grafted cationic hydrogels in an environment of changing pH", Biomaterials, 21(14):1439-50 (2000).
Podual, et al., "Glucose-sensitivity of glucose oxidase-containing cationic copolymer hydrogels having poly(ethylene glycol) grafts", J. Con. Rel. 67:9-17 (1999).
Ravaine, et al., "Chemically controlled closed-loop insulin delivery", J. Control Release, 132:2-11 (2008).
Yan, et al., "Encapsulation of single enzyme in nanogel with enhanced biocatalytic activity and stability", J. Am. Chem. Soc., 128:11008-9 (2006).
Zhang, et al., "A novel route to prepare pH- and temperature-sensitive nanogels via a semibatch process", J. Colloid and Interface Sci., 330:330-6 (2009).

* cited by examiner

*Primary Examiner* — Julie Ha
*Assistant Examiner* — Kristina M Hellman
(74) *Attorney, Agent, or Firm* — Pabst Patent Group LLP

(57) ABSTRACT

Injectable insulin loaded microgels that are capable of modifying the amount of insulin released based on the patient's tissue glucose levels, methods for making and using these compositions have been developed. The microgels contain insulin, glucose oxidase entrapped in or bound to the microgels, and an agent that reduces hydrogen peroxide, entrapped in or bound to the microgels, wherein the polymeric microgel expands when pH decreases from physiological pH and shrinks when pH increases towards physiological pH, thereby releasing insulin at a rate corresponding to the glucose concentration. In one embodiment, the glucose oxidase and/or the agent reducing hydrogen peroxide are encapsulated in nanogels, then encapsulated within the microgel.

11 Claims, 9 Drawing Sheets

GLUCOSE-RESPONSIVE MICROGELS FOR CLOSED LOOP INSULIN DELIVERY

CROSS-REFERENCE TO RELATED APPLICATIONS

This application is an application under 35 U.S.C. §371 of copending PCT Application No. PCT/US2013/026633, filed Feb. 19, 2013, which claims benefit of U.S. Provisional Application No. 61/600,394, filed Feb. 17, 2012.

FIELD OF THE INVENTION

The present invention generally relates to glucose-responsive formulations containing insulin for the treatment of diabetes.

STATEMENT REGARDING FEDERALLY SPONSORED RESEARCH

The U.S. government has no rights in this invention.

BACKGROUND OF THE INVENTION

Diabetes mellitus is a disorder of glucose regulation with accumulation of glucose in the blood. It is a major public health problem affecting 285 million people across the world and this number is expected to be over 450 million by 2030 (Wild, et al., *Diabetes care,* 27:1047-1053 (2004). The malfunction of glucose regulation arises from 1) insufficient secretion of insulin due to autoimmune-mediated destruction of pancreatic, a-cells (type 1 diabetes) or 2) disorders of both insulin resistance and secretion (type 2 diabetes) (Pickup, et al., *Diabetes Metab Res Rev,* 24: 604-610 (2008); Stumvoll, et al. *Lancet,* 365:1333-1346 (2005); and Kahn, *Diabetes* 43:1066-1084 (1994).

Multiple subcutaneous insulin injections and regular monitoring of blood glucose levels are thus essential to sustain life for type 1 diabetic patients and some type 2 diabetic patients (Owens, et al., *Lancet,* 358:739-746 (2001). However, such self-administration is painful and requires an indispensable commitment of patients. More importantly, this treatment, known as open-loop insulin delivery, does not maintain normoglycemia upon the blood glucose fluctuation (Jeandidier, et al., *Adv Drug Deliv Rev,* 35:179-198 (1999); Owens, et al., *Nat Rev Drug Discov,* 1:529-540 (2002)). Lack of tight control of glucose closer to the normal level accounts for many chronic complications such as limb amputation, blindness and kidney failure and often resulted in risks of fatal hypoglycemia (*N Engl J Med.,* 329:977-986 (1993). Therefore, an artificial pancreas-like synthetic closed-loop device able to continuously and intelligently release insulin with the response to blood glucose levels is highly desirable (Kumareswaran, et al. *Expert Rev Med Devices,* 6:401-410 (2009); Ravaine, et al., *J. Control Release,* 132:2-11 (2008)). A straightforward strategy is to integrate a glucose monitoring moiety and a sensor-triggered insulin releasing moiety into one system (Ravaine, et al., *J. Control Release* 132:2-11 (2008)).

A glucose oxidase (GOx) based system which is made of a compartment limited by a semipermeable, ionically charged membrane, containing insulin, glucose oxidase and catalase is described for example in U.S. Pat. No. 4,364,385 to Lossef, et al. WO 06/088473 describes an insulin delivery system in which glucose oxidase, catalase, and insulin are entrapped in, dispersed within, covalently bonded to or embedded within nanospheres to generate a glucose-responsive insulin-delivery vehicle. Glucose Oxidase has also been immobilized onto pH-sensitive hydrogels (Podual, *J. Con. Rel.* 67:9-17 (1999); Ravaine, *J. Controlled Rel.,* 132:2-11 (2008)). The conversion of glucose to gluconic acid, catalyzed by glucose oxidase, lowers the pH affecting the swelling of pH sensitive hydrogels. This swelling allows a release of insulin in response to an increase in glucose concentrations in the immediate environment.

To effectively control diabetes and prevent hypoglycemic complications, it is desirable to administer insulin in a manner that precisely matches the physiological needs at any given moment. Known hydrogel glucose oxidase-dependent systems suffer from several limitations. For example, hydrogel systems exhibit very long glucose response times. Ravaine, et al., *J. Controlled Rel.,* 132:2-11 (2008). Thus, there still is a significant need for insulin that can become physiologically available as a result of changes in the body's glucose levels.

It is therefore an object of this invention to provide an insulin delivery system that is responsive to changing glucose concentrations at or near physiological pH.

It is also an object of the present invention to provide a method of making a glucose sensitive insulin delivery system that is responsive to glucose concentrations at or near physiological pH.

It is a further objection of the present invention to provide a method of controlling blood glucose levels in a patient in need thereof.

SUMMARY OF THE INVENTION

Injectable insulin loaded microgels that are capable of controlling the amount of insulin released based on the patient's tissue glucose levels, and methods for making and using these compositions, have been developed. The microgels serve as artificial islet-cell equivalents to effectively release encapsulated insulin in a glucose-responsive fashion. In one embodiment, the microgels contain a glucose oxidizing agent, a pH-responsive polymeric scaffold, such as a physically cross-linked pH-responsive polymeric matrix, and exogenous insulin, such as human recombinant insulin.

The glucose oxidizing agent is preferably an enzyme, for example, glucose oxidase (GOx). The microgel can additionally contain an agent that can regenerate $O_2$ and/or reduce hydrogen peroxide, for example, a catalase or peroxidase. Continuous swelling leads to expansion and dissociation of the polymeric network, which in turn triggers insulin release. Additionally, the acidic environment increases the solubility of insulin, further increasing the insulin release rate. Importantly, this system is reversible and under normoglycemic conditions, the microgels shrink and insulin release is ceased.

In some embodiments, the enzymes (but not insulin) are encapsulated in a polymeric nanocapsule to enhance enzymatic stability, avoid denaturation, shield immunogenicity, and/or attenuate diffusion from the microgel matrix. Insulin can also be encapsulated in the nanocapsules or can be independently encapsulated in nanoparticles in order to adjust the release rate. Embodiments in which the enzymes and insulin are loaded directly into the microgels without employing nanocapsules are also described herein. The nanocapsules can be prepared via interfacial polymerization, such as with acrylamide, N-(3-aminopropyl)methacrylamide, and N,N'-methylene bisacrylamide. The polymerization can be initiated with a free radical initiator, such as ammonium persulfate (APS) and/or 1,2-bis(dimethylamino)ethane (TEMED). Other free radical initiators can also be used.

The microgels can be formulated for subcutaneous, intradermal or intramuscular administration. In one embodiment, the formulations are administered via subcutaneous injection. Injectable formulations contain insulin-loaded microgels in a sterile pharmaceutically suitable diluent for injection.

DETAILED DESCRIPTION OF THE INVENTION

I. Definitions

Figure 1A:
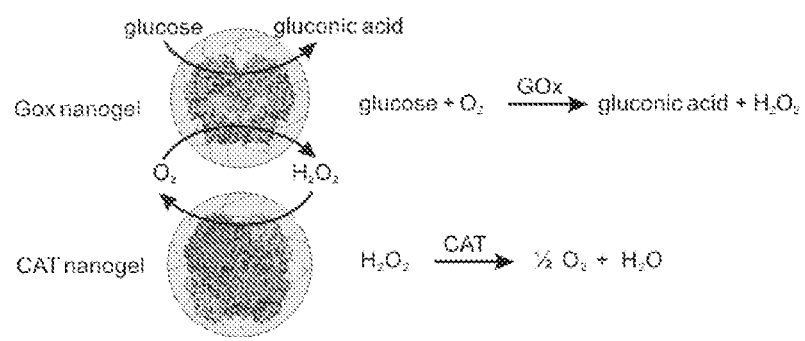
FIG. 1A is a schematic of glucose-responsive microgels encapsulated with insulin and enzyme nanogels. Protonation of amines within the polymer increases the hydrogel's charge, causing the microgel to swell.

"Biocompatible" as used herein, generally refers to a material and any metabolites or degradation products thereof that are generally non-toxic to the recipient and do not cause any significant adverse effects to the subject.

"Biodegradable" as used herein, generally refers to a material that will degrade or erode under physiologic conditions to smaller units or chemical species that are capable of being metabolized, eliminated, or excreted by the subject. The degradation time is a function of polymer composition and morphology. Suitable degradation times are from days to weeks. For example, the polymer may degrade over a time period from seven days to 24 weeks, preferably seven days to twelve weeks, more preferably seven days to six weeks, most preferably from seven days to three weeks.

"Controlling blood glucose levels" refers to the maintenance of blood glucose concentrations at a desired level, typically between 70-130 mg/dL or more preferably 90-110 mg/dL.

"Dosage unit form" as used herein refers to a physically discrete unit of conjugate appropriate for the patient to be treated.

"Excipient" as used herein, generally includes any pharmaceutically or biologically acceptable compound that can be contained in, on, or in combination with microgels.

"Microgel" as used herein refers to particles of gel of any shape, formed of covalently cross-linked polymeric networks, having an average diameter of approximately 100 to 500 µm, such as about 100, 125, 150, 175, 200, 225, 250, 275, 300, 325, 350, 375, 400, 425, 450, 475, or 500 µm. "Microgels" are used interchangeably herein with "microparticles", to refer to particles within the disclosed size range, made of a covalently crosslinked polymeric network, (i.e., gel).

The term "diameter" is art-recognized and is used herein to refer to either the physical diameter or the hydrodynamic diameter. The diameter of an essentially spherical particle may refer to the physical or hydrodynamic diameter. The diameter of a nonspherical particle may refer preferentially to the hydrodynamic diameter. As used herein, the diameter of a non-spherical particle may refer to the largest linear distance between two points on the surface of the particle. When referring to multiple particles, the diameter of the particles typically refers to the average diameter of the particles. Particle diameter can be measured using a variety of techniques in the art including, but not limited to, dynamic light scattering.

"Monodisperse" is used herein to describe a population of particles where all of the particles are the same or nearly the same size. For example, "monodisperse" refers to particle distributions in which 90% of the distribution lies within 15% of the median particle size, more preferably within 10% of the median particle size, most preferably within 5% of the median particle size.

"Nanocapsule", as used herein, refers to a nano-sized particle or capsule having a core that is surrounded by a shell (i.e., a hollow core). Nanocapsule is used herein interchangeably with nanogel or nanoparticle. "Nanocapsule," as used herein, generally refers to a particle of any shape having a diameter from about 1 nm up to, but not including, about 1 micron, preferably from about 5 nm to about 500 nm, more preferably from about 5 nm to about 100 nm, most preferably from about 5 nm to about 50 nm, such as about 5, 10, 15, 20, 25, 30, 35, 40, 45, or 50 nm.

"Insulin analog" as used herein refers to human insulin in which one or more amino acid residues have been replaced by another amino acid residue or deleted or in which the A chain and/or the B chain has been extended by addition of one or more amino acid residues at the N-terminal or at the C-terminal and which functions to replace endogenous insulin. Insulin analogs will typically have different pharmacokinetics than endogenous insulin. Unless specified otherwise, "insulin" refers to recombinant human insulin and analogs thereof. Dosages may be optimized based on the pharmacokinetics of the insulin analog relative to human insulin based on known pharmacokinetics by one of skill in the art.

II. Compositions

Insulin-loaded microgels which controllably release the insulin in response to blood glucose levels are made glucose-sensing by including agents that oxidize glucose to produce gluconic acid, hydrogen ions and hydrogen peroxide. The microgels can further contain agents that reduce the hydrogen peroxide to produce oxygen and water (See FIG. 1A). Taken together, the insulin-loaded microgels function like a smart valve system-high glucose levels cause the pH to decrease, which makes the hydrogel expand, thereby promoting insulin release, and low glucose levels allow the pH to equilibrate towards physiological pH, which makes the hydrogel shrink, thereby decreasing insulin release (See FIG. 1B). When the glucose level increases, the microgels expand, releasing insulin. Conversely, when the glucose level decreases, causing the pH to rise, the microgels shrink and the insulin release is inhibited. In some embodiments, the insulin release profile exhibits a prominent pulsatile pattern: with a high release rate at a hyperglycemic level (e.g., 400 mg/dL) and low release rate at a normal level (e.g., 100 mg/dL), which is highly desirable for self-regulation-based closed loop delivery systems.

Additionally, the microgels exhibit a quick responsive switch of release upon exposure to hyperglycemic glucose levels. For example, the first responsive point is at 30 min upon addition of 400 mg/dL glucose. Preliminary data has validated that the released insulin within the first 30 min can effectively decrease the blood glucose levels in mice. The response speed can be adjusted by changing the amount of enzymes and the crosslink density of the polymer matrix, e.g., chitosan. For example, increasing the ration of enzymes to encapsulated insulin or decreasing the crosslink density will increase the response speed. In vivo, the total released amount of insulin can be tuned by injected doses.

The quick responsive switch of release rate from hyperglycemic level to normal level allows tight control of glucose close to normal blood glucose levels. Meanwhile, a long-term release of insulin can also be realized. The microgels retain substantial activity and insignificant release of insulin in 1×PBS (physiological PBS) stock solution at 4° C. for at least two months.

A. Microgels

Figure 1B:
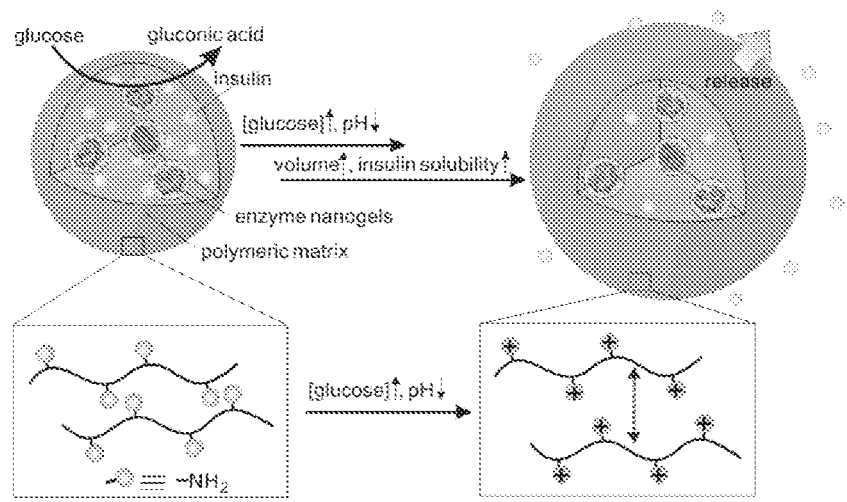
FIG. 1B is a schematic showing the enzymatic reactions through glucose oxidase (GOx) and catalase (CAT) encapsulated nanogels.

Exemplary microgels are shown in FIG. 1B. The microgels include three components: (1) a glucose oxidizing agent; (2) a pH-responsive polymeric scaffold, such as a cross-linked pH-responsive polymeric matrix; (3) and exogenous insulin, such as human recombinant insulin.

In particular embodiments, the pH-responsive polymeric matrix is a crosslinked pH-responsive polymeric matrix. In more particular embodiments, the polymeric matrix is non-covalently crosslinked, such as through strong electrostatic interactions (e.g., ionic crosslinking) or weaker electrostatic interactions (e.g., hydrogen-bonding).

The polymer matrix encapsulates a glucose oxidizing agent. In particular embodiments, the glucose oxidizing agent is an enzyme, such as glucose oxidase (GOx), which oxidizes glucose to produce hydrogen peroxide and D-glucono delta lactone, the cyclic form of gluconic acid The glucose oxidase enzyme (GOx) (EC 1.1.3.4) is an oxido-reductase that catalyses the oxidation of glucose to hydrogen peroxide and D-glucono-δ-lactone. In cells, it aids in breaking the sugar down into its metabolites.

The microgel can further contain a material which produces or provides oxygen to assist the oxidation of glucose by GOx and/or reduces the hydrogen peroxide. Suitable materials include, but are not limited to, catalase (CAT). The glucose oxidizing agent and any additional agents used to facilitate glucose oxidation can be encapsulated in order to protect the agents and maintain their activity. For example, agents can be encapsulated in nanocapsules. The formation of gluconic acid generate pH stimulus, for example, lowers pH which protonates basic groups on the polymer increasing the amount of positive charge causing the polymer to swell and releasing insulin.

The bulk scaffold that forms the microgel can be one or more biocompatible synthetic and/or natural polymers. In particular embodiments, the polymers are biocompatible and biodegradable. Useful materials include pH-sensitive polymers, which respond to changes in pH of the external environment, in part due to the presence of side groups or side chains which are readily ionizable. In particular embodiments, the hydrogels expand at less than physiological pH and shrink at physiological pH. In some embodiments, the polymer contains amine-rich units, which can be readily protonated upon formation of acid and subsequently trigger swelling of the entire matrix. The subsequent expansion of the matrix pore size facilitates release of insulin. Meanwhile, the solubility of insulin will be increased under acidic environment, which further increases insulin release rate.

Some pH sensitive polymers useful in making pH-responsive microgels include, but are not limited to, chitosan, polymethyacrylic acid (PAA), polymethyl methacrylate (PMMA), polyacrylamide (PAAm), polydimethyl-aminoethylmethacrylate (PDEAEMA) and polyethylene glycol. Other pH-sensitive polymers include terpolymers of N-vinyl-2-pyrrolidone, methacrylamide, and itaconic acid, polydimethylaminoethylmethacrylate, polyethyleneglycol, copolymer of polymethacrylic acid and polyethylene glycol, copolymer of cationic guar gum and acrylic acid monomer. U.S. Pat. No. 7,683,041 describes microgels which are responsive to mild acidic conditions. Zhang, et al., *J. Colloid and Interface Sci.*, 330:330-336 (2009) describes pH-sensitive nanogels made from N-iropropylacrylamide (NIPAM) and acrylic acid.

Other useful polymers include alginate, which can also be non-covalently crosslinked, for example, by positively charged ions, such as calcium ions. Microgels made of alginate shrink, instead of swell, in response to changes in physiological glucose levels.

In one embodiment, the microgel is prepared from chitosan. In the body, chitosan is degraded by ubiquitous lysozymes or glycosidases into amino sugars and subsequently cleared from the body.

In some embodiments, the chitosan can be non-covalently crosslinked, such as by electrostatic interactions. Ionically crosslinked chitosan hydrogels typically exhibit a higher swelling sensitivity to pH changes compared to covalently crosslinked chitosan hydrogels.

In particular embodiments, the crosslinking agent is negatively charged, i.e., anionic. Suitable electrostatic or ionic crosslinking agents include, but are not limited to, tripolyphosphate (TPP), glycerol phosphate disodium salt (GP), sodium sulfate, and b-glycerophosphate. In one embodiment, chitosan is crosslinked with tripolyphosphate (TPP). The structures for chitosan and TPP are shown below.

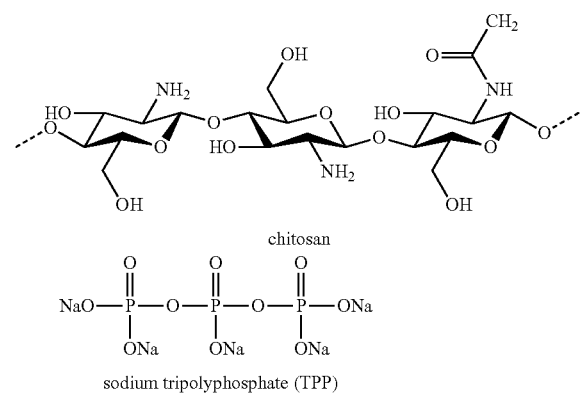

Preferably, the TPP solution is used to crosslink chitosan at about 5%-15% by weight TPP, preferably 5%-10% by weight TPP, more preferably 5%-8% by weight TPP, most preferably 5%-6% by weight TPP.

Crosslinking density can affect the properties of ionically crosslinked hydrogels, such as mechanical strength, swelling and drug release. The crosslinking reaction is mainly influenced by the size of the crosslinker and the charges of the polymer (e.g., chitosan) and crosslinker during the reaction. The smaller the size of the crosslinker, typically the faster the crosslinking reaction, since diffusion is easier and more rapid. The charge densities of the polymer and the crosslinker should be sufficiently high to facilitate interaction and formation of a hydrogel. In particular embodiments, the crosslinker has a high charge density, ensuring a high crosslinking density, such as tripolyphosphate. Crosslinking should be incomplete in order to allow a pH-dependent swelling with such crosslinkers. This can be achieved by a short reaction time and a low crosslinker concentration. Another possibility for obtaining networks which are mechanically stable but with high swelling and drug release, is the combination of different crosslinkers, such as citrate and tripolyphosphate.

The microgel particle size may vary between about 100 to 1000 μm, such as about 100, 150, 200, 250, 300, 350, 400, 450, 500, 550, 600, 650, 700, 750, 800, 850, 900, 950, or 1000 microns. In some embodiments, the microgels have an average diameter from about preferably from about 100 to 800 μm, 100 to 500 μm, 100 to 400 μm, or 100 to 300 μm and exhibit a loading efficiency of at least about 20%, 25%, 30%, 35%, 40%, 45%, 50%, 55%, or 60% by weight. In some embodiments, the loading efficiency is at least about 40%, such as greater than 41%, 42%, 43%, 44%, 45%, 46%, 47%, 48%, 49%, 50%, 51%, 52%, 53%, 54%, 55%, 56%, 57%, 58%, 59%, or 60% by weight.

B. Nanocapsules

The microgels contain insulin, a glucose oxidizing agent and optionally a hydrogen peroxide-reducing agent. In particular embodiments, the glucose oxidizing agent and optional hydrogen peroxide reducing agents are enzymes. In more particular embodiments, the glucose oxidizing agent and optional hydrogen peroxide reducing agents are encapsulated in a nanocapsule or nanogel, such as a polymeric nanocapsule or nanogel. The loading capacity of the nanocapsules/nanogels in the microgel is preferably about 20, 25, 30, 35, 40, 45, or 50% by weight.

The nanocapsule is formed of one or more biocompatible synthetic polymers or natural polymers, preferably, polymers which are biocompatible and biodegradable. Examples, of biocompatible polymers include, but are not limited to chitosan, alginate, dextran, hyaluronic acid, acrylamides, and PLGA. Examples of biodegradable polymers include but are not limited to the biocompatible polymers listed above and any other synthetic or natural polymers linked with ester, disulfide or enzymatically cleavable structures. In some embodiments, the nanocapsules/nanogels are formed of an acrylamide.

The average diameter of the nanocapsule can vary from about 5 nm to about 500 nm, preferably about 5 nm to about 250 nm, more preferably from about 5 nm to about 200 nm, most preferably from about 5 nm to about 100 nm. Typically, for "single protein nanocapsules", the size ranges from about 5 nm to about 50 nm, preferably from about 5 nm to about 40 nm, about 5 nm to about 35 nm, about 5 nm to about 30 nm, about 5 nm to about 25 nm, about 5 nm to about 20 nm. In particular embodiments, the average diameter is from about 8 to about 30 nm, preferably from about 8 nm to about 25 nm.

The nanocapsule encapsulates glucose oxidizing enzymes and hydrogen peroxide reducing enzymes. The glucose can diffuse into enzyme nanocapsules through the porous polymeric shell and be catalyzed by glucose oxidase to generate D-glucono-1,5-lactone, which then hydrolyzes to gluconic acid. See FIGS. 1A and 1B.

Nanocapsules are preferably made using acrylamide as the monomer, cross-linked with N,N'-methylene bisacrylamide are described in Yan, et al., *J. Am. Chem. Soc.*, 128:11008-11009 (2006). The enzymes are individually encapsulated in the "single protein nanocapsule" as described, for example, in Yan, et al., *J. Am. Chem. Soc.*, 128:11008-11009 (2006)). The polymeric shell of each nanocapsule is covalently (chemically) linked to the surface of enzymes. Emulsion or double emulsion methods can also be used to prepare enzyme nanocapsules.

C. Therapeutic Agents and Enzymes

Glucose-Oxidizing and Hydrogen Peroxide Reducing Agent

Agents which can oxidize glucose are known in the art and preferably are enzymes, for example, glucose oxidase. Similarly, agents capable of reducing hydrogen peroxide are known in the art. Preferably the peroxide reducing agent is an enzyme, for example, a peroxidase. Examples include catalase and glutathione peroxidase. The glucose oxidizing and hydrogen peroxide reducing enzymes are preferably covalently encapsulated into nanocapsules crosslinked by a redox-degradable crosslinker to enhance enzymatic stability, avoid denaturation, shield immunogenicity and attenuate diffusion from polymeric matrix.

In some embodiments, the enzymes are embedded in the matrix of nanocapsules. In other embodiments the enzymes are encapsulated inside the nanocapsule. The loading yield of each enzyme is between about 20-50% by weight. The loading weight ratio of enzymes to insulin is between about 1:2, 1:3 to 1:10. In a preferred embodiment it is about 1:8.

Insulin

Any insulin may be included in the formulation. Typically the formulation contains from 5 to 1,000 U of insulin/ml of formulation, preferably 100 U of insulin/ml of formulation, typically greater than 20 U of insulin/ml of the formulation. Preferably, the amount of insulin is effective to control the recipient's blood glucose levels. Preferably, insulin is included at a loading capacity of about 51.5%, which can be adjusted by tuning the crosslinker density and the size of microgels. The dosage unit of microgels is preferably between 100 U of insulin/mL to 400 U/mL.

The insulin may be human insulin, recombinant human insulin, insulin from a non-human animal source (e.g. bovine, porcine) or any other insulin, including insulin analogs. The preferred insulin is of the same species as the receipient—i.e., human insulin for treatment of humans. The insulin formulations can include mixtures of different insulins. Representative insulins include:

Fast Acting Insulins

Fast acting insulins start to work within one to 20 minutes, peaking about one hour later and lasting from three to five hours. Fast acting insulin takes about two hours to fully absorb into the systemic circulation. Fast acting insulins include regular recombinant human insulin (such as HUMULIN® marketed by Lilly, and NOVOLIN®, marketed by NovoNordisk) which are administered in an isotonic solution at pH 7. Bovine and porcine insulins, which differ in several amino acids to human insulin, but are bioactive in humans, are also fast acting insulins.

Rapid Acting Insulin

This group includes insulins that have been modified or have altered locations of amino acids in order to enhance their rate of absorption. There are three types of rapid-acting commercial insulin analogs available: lispro insulin (Lysine-Proline insulin, sold by Eli Lilly as HUMALOG®), glulisine insulin (sold by Sanofi-Aventis as APIDRA® and aspart insulin (sold by Novo Nordisk as NOVOLOG®)

Intermediate Acting Insulins

Intermediate-acting insulin has a longer lifespan than short-acting insulin but it is slower to start working and takes longer to reach its maximum strength. Intermediate-acting insulin usually starts working within 2-4 hours after injection, peaks somewhere between 4-14 hours and remains effective up to 24 hours. Types of intermediate-acting insulin include NPH (Neutral Protamine Hagedorn) and LENTE® insulin. NPH insulin contains protamine which slows down the speed of absorption so that the insulin takes longer to reach the bloodstream but has a longer peak and lifespan.

Long Acting Insulins

Long acting insulins include Eli Lilly's Humulin® U (Ultralente® human insulin (recombinant DNA origin) extended zinc suspension); and insulin glargine (Lantus® Aventis). Insulin glargine is a recombinant human insulin analog that can have up to 24 hour duration. It differs from human insulin by having a glycine instead of asparagine at position 21 and two arginines added to the carboxy-terminus of the beta-chain. LANTUS® consists of insulin glargine dissolved in a clear aqueous fluid (100 IU, 3.6378 mg insulin glargine, 30 micrograms zinc, 2.7 mg m-cresol, 20 mg glycerol 85%, and water to 1 ml).

Other Pharmaceutically Active Agents

Insulin may be administered alone or in combination with other pharmaceutical agents. Macromolecules such as proteins/peptides can be encapsulated in the microgel with an expected high yield. Small drugs can be encapsulated in some nanocapsules using biocompatible/degradable polymers and then embedded inside microgels. The embedded drugs can also be organic-soluble, which can be dissolved in suitable solvent and mixed with materials to make microgels (such as chitosan). The final mixture for electrospray can be an emulsion-like solution.

Examples of agents that can be delivered in combination with insulin include other peptides or proteins. Preferably, the active agent is at least slightly soluble in aqueous medium (i.e. 10,000 parts of aqueous solvent per solute), and more preferably is highly soluble in aqueous medium. Suitable peptides include C-peptide; glucagon-like peptide 1 (GLP 1) and active fragments thereof; human amylin and synthetic forms of amylin such as pramlintide; parathyroid hormone (PTH) and active fragments thereof (e.g. $PTH_{1-34}$); calcitonin; human growth hormone (HGH); erythropoietin (EPO); macrophage-colony stimulating factor (M-CSF); granulocyte-macrophage-colony stimulating factor (GM-CSF); and interleukins.

Suitable small molecules include nitroglycerin, sumatriptan, narcotics (e.g. fenatnyl, codeine, propoxyphene, hydrocodone, and oxycodone), benzodiazepines (e.g. Alprazolam, Clobazam, Clonazepam, Diazepam Flunitrazepam, Lorazepam, Nitrazepam, Oxazepam, Temazepam, and Triazolam), phenothiazines (Chlorpromazine, Fluphenazine, Mesoridazine, Methotrimeprazine, Pericyazine, Perphenazine, Prochlorperazine, Thioproperazine, Thioridazine, and Trifluoperazine), and selective serotonin reuptake inhibitors (SSRIs) (e.g. sertraline, fluvoxamine, fluoxetine, citalopram, and paroxetine).

D. Dosage Forms

The insulin formulations are preferably formulated in dosage unit form for ease of administration and uniformity of dosage.

The insulin-loaded microgel may be combined with one or more pharmaceutically acceptable carriers to form a pharmaceutical composition. As would be appreciated by one of ordinary skill in this art, the carriers are chosen based on the route of administration as described below, the location of the target tissue, the drug being delivered, the time course of delivery of the drug, etc. Suitable excipients include surfactants, emulsifiers, emulsion stabilizers, anti-oxidants, emollients, humectants, suspending agents, thickening agents, occlusive agents, preservatives, stabilizing agents, pH modifying agents, solubilizing agents, solvents, colorants, isotonicity providing agents and other excipients.

The insulin-loaded microgels may be administered as an admixture or mixture with one or more pharmaceutically acceptable carriers, excipients or diluents for injection. Suitable dosage forms include powders, films, capsules and injectable formulations. Injectable formulations can be administered subcutaneously, intramuscularly, or intradermally. In a preferred embodiment, the formulation is injected subcutaneously. In this embodiment the insulin-loaded hydrogel is provides as a liquid formulation suitable for injection. In another embodiment, the formulation is formed by mixing a powdered active agent with a liquid diluent that contains a pharmaceutically acceptable liquid carrier and one or more solubilizing agents. The insulin-loaded microgels can be provided in lyophilized form in one compartment of a kit, such as a vial, and the liquid component, i.e. the diluent, is provided in a second compartment, such as a second vial. Optionally, one or more excipients are present in one or both vials, as appropriate to adjust pH, and stabilize and buffer the formulation. Preferably, the injectable formulations include a mono-dispersed plurality of particles. For example, the formulation contains a particle distribution in which about 90% of the distribution lies within 5% of the median particle size.

The ability of a particular insulin formulation to release insulin as a function of glucose levels can be assessed by a suitable experiment, such as but not limited to in vitro glucose challenge experiments, dissolution experiments with release media containing glucose levels at 150 mg/dl or above, or in a diabetic animal model, such as but not limited to diabetic swine, diabetic mice, diabetic rat, or diabetic dog.

III. Methods of Making the Compositions

Methods for making nanocapsules and microgels are known in the art and include, but are not limited to, spray drying, interfacial polymerization, phase separation encapsulation (spontaneous emulsion microencapsulation, solvent evaporation microencapsulation, and solvent removal microencapsulation) and coacervation. A brief summary of these methods is presented below.

A. Methods of Making Microgels

Microgels fabricated as described herein are preferably geometrically uniform and can be directly administrated through subcutaneous injection. Additionally, loading yield of payload (insulin) through microgels is high (i.e., about ~60%).

1. Spray Drying

Methods for forming microspheres/nanospheres using spray drying techniques are described in U.S. Pat. No. 6,620,617, to Mathiowitz et al. In this method, the polymer is dissolved in an organic solvent such as methylene chloride or in water. A known amount of one or more active agents to be incorporated in the particles is suspended (in the case of an insoluble active agent) or co-dissolved (in the case of a soluble active agent) in the polymer solution. The solution or dispersion is pumped through a micronizing nozzle driven by a flow of compressed gas, and the resulting aerosol is suspended in a heated cyclone of air, allowing the solvent to evaporate from the microdroplets, forming particles. Microspheres/nanospheres ranging between 0.1-10 microns can be obtained using this method.

2. Interfacial Polymerization

Interfacial polymerization can also be used to encapsulate one or more active agents. Using this method, a monomer and the active agent(s) are dissolved in a solvent. A second monomer is dissolved in a second solvent (typically aqueous) which is immiscible with the first. An emulsion is formed by suspending the first solution through stirring in the second solution. Once the emulsion is stabilized, an initiator is added to the aqueous phase causing interfacial polymerization at the interface of each droplet of emulsion.

3. Phase Separation Microencapsulation

In phase separation microencapsulation techniques, a polymer solution is stirred, optionally in the presence of one or more active agents to be encapsulated. While continuing to uniformly suspend the material through stirring, a nonsolvent for the polymer is slowly added to the solution to decrease the polymer's solubility. Depending on the solubility of the polymer in the solvent and nonsolvent, the polymer either precipitates or phase separates into a polymer rich and a polymer poor phase. Under proper conditions, the polymer in the polymer rich phase will migrate to the interface with the continuous phase, encapsulating the active agent(s) in a droplet with an outer polymer shell.

a. Spontaneous Emulsion Microencapsulation

Spontaneous emulsification involves solidifying emulsified liquid polymer droplets formed above by changing temperature, evaporating solvent, or adding chemical cross-linking agents. The physical and chemical properties of the encapsulant, as well as the properties of the one or more active agents optionally incorporated into the nascent particles, dictates suitable methods of encapsulation. Factors such as hydrophobicity, molecular weight, chemical stability, and thermal stability affect encapsulation.

b. Solvent Evaporation Microencapsulation

Methods for forming microspheres using solvent evaporation techniques are described in E. Mathiowitz et al., *J. Scanning Microscopy*, 4:329 (1990); L. R. Beck et al., *Fertil. Steril.*, 31:545 (1979); L. R. Beck et al *Am J Obstet Gynecol* 135(3) (1979); S. Benita et al., *J. Pharm. Sci.*, 73:1721 (1984); and U.S. Pat. No. 3,960,757 to Morishita et al. The polymer is dissolved in a volatile organic solvent, such as methylene chloride. One or more active agents to be incorporated are optionally added to the solution, and the mixture is suspended in an aqueous solution that contains a surface active agent such as poly(vinyl alcohol). The resulting emulsion is stirred until most of the organic solvent evaporated, leaving solid microspheres/nanospheres. This method is useful for relatively stable polymers like polyesters and polystyrene. However, labile polymers, such as polyanhydrides, may degrade during the fabrication process due to the presence of water. For these polymers, some of the following methods performed in completely anhydrous organic solvents are more useful.

4. Coacervation

Procedures for encapsulation using coacervation techniques are known in the art, for example, in GB-B-929 406; GB-B-929 401; and U.S. Pat. Nos. 3,266,987, 4,794,000, and 4,460,563. Coacervation involves the separation of a macromolecular solution into two immiscible liquid phases. One phase is a dense coacervate phase, which contains a high concentration of the polymer encapsulant (and optionally one or more active agents), while the second phase contains a low concentration of the polymer. Within the dense coacervate phase, the polymer encapsulant forms nanoscale or microscale droplets. Coacervation may be induced by different methods including a temperature change, addition of a nonsolvent or addition of a micro-salt (simple coacervation), or by the addition of another polymer thereby forming an interpolymer complex (complex coacervation).

The amount of microgels needed to deliver a pharmaceutically effective dosage of insulin in a patient will vary based on such factors including but not limited to, the crosslinker and polymerizing group chosen, the protein loading capacity and efficiency of the gel particles, the toxicity levels of the biodegraded particles, the amount and type of bioactive material needed to effect the desired response, the subject's species, age, weight, and condition, the disease and its severity, the mode of administration, and the like. One skilled in the art would be able to determine the pharmaceutically effective dosage.

B. Methods of Making Nanocapsules

The nanocapsules can be made using methods known in the art, for example, as reviewed in Gu et al, "Tailoring Nanocarriers for Intracellular Protein Delivery" *Chemical Society Reviews*, 40:3638-3655 (2011).

In one embodiment, the glucose-oxidizing enzyme and the hydrogen peroxide reducing enzymes are encapsulated into a nanocapsule as described for example in Yan, et al., *J. Am. Chem. Soc.*, 128:11008-11009 (2006). The enzymes can be encapsulated through interfacial polymerization with acrylamide, N-(3-aminopropyl)methacrylamide and N,N-methylene bisacrylamide). For example, Compact nanocapsules were prepared following the free radical polymerization in an aqueous solution containing monomers (acrylamide (AAm) and N-(3-aminopropyl)methacrylamide (APMAAm)) and crosslinker (N,N'-methylene bisacrylamide). Enzyme nanocapsules were spherical and uniform in size, with a diameter of ~12 nm as determined by the transmission electron microscopy (TEM) and dynamic light scattering (DLS) analysis. The Circular Dichroism (CD) spectra of the native and the enzyme nanocapsules confirmed that the enzymes retained the secondary structure of native proteins.

Nanocapsules can also be prepared using emulsion-based encapsulation. Particles can be prepared using an inverse microemulsion technique where the aqueous phase (monomer, protein, and crosslinker) is dispersed via sonication in the organic phase. Addition of a free radical initiator results in polymerization around the protein to form water-soluble nanoparticles. In situ polymerization based encapsulation can also be used to make the nanocapsules. Briefly, polymerizable vinyl groups are covalently linked to the enzyme; subsequently, polymerization is performed in an aqueous solution containing monomers and crosslinker to wrap each protein core with a thin polymer shell that can protect the protein content from denaturation and proteolysis. This scheme enabled the synthesis of protein nanocapsules with non-degradable or degradable shells by using a non-degradable or degradable crosslinker (Table 1), respectively.

Another useful method for making nanoparticles is the phase inversion nanoencapsulation (PIN) method. In this method a polymer is dissolved in a "good" solvent, fine particles of a substance to be incorporated are mixed or dissolved in the polymer solution, and the mixture is poured into a strong non-solvent for the polymer, to spontaneously produce, under favorable conditions, polymeric nanospheres, wherein the polymer is either coated with the particles or the particles are dispersed in the polymer. See, e.g., U.S. Pat. No. 6,143,211 to Mathiowitz, et al.

The encapsulated or immobilized enzymes retain a significantly higher percent activity than the non-encapsulated native enzyme. For example, at 60° C., the encapsulated enzyme retains at least 40 to 75% of its activity after 30 minutes, one hour, 90 minutes, 2 hours, 3 hours, 4 hours, 5 hours, or 6 hours compared to the non-encapsulated native enzyme, as described in the examples. This stability can be achieved by covalently attaching the polymer to the enzyme or by non-covalent association of the polymer with the enzyme. In particular embodiments, the polymer is covalently associated with the enzymes.

The nanocapsules loaded with enzymes are encapsulated in a pH responsive microgel, preferably by electrospraying. Enzyme activity after encapsulation of the nanocapsule in the microgel, is at least 40 to 85% compared to the native enzyme after 30 minutes, one hour, 90 minutes, 2 hours, 3 hours, 4, hours, or 5 hours, as shown in the examples.

IV. Methods of Using the Compositions

The formulations may be administered via different routes, preferably by injection, most preferably subcutaneous administration, but could be administered by intradermal or intramuscular injection.

In some embodiments, prior to injection, the formulation is in the form of an insulin suspension. Optionally, the insulin-loaded microgels are provided in lyophilized form in one compartment of a kit, such as a vial, and the liquid component, i.e. the diluent or suspending fluid, is provided in a second compartment, such as a second vial. Optionally, one or more excipients are present in one or both vials, as appropriate to adjust pH, and stabilize and buffer the formulation.

In one embodiment, the formulation is an insulin formulation designed to release insulin into systemic circulation over time with a basal release profile following injection into a patient. In another embodiment, the formulation is designed to release insulin into systemic circulation over time with a non-basal release profile following injection in a patient. Exemplary non-basal release profiles include a regular human insulin release profile and a prandial release profile. In one embodiment the formulation is designed to release insulin into systemic circulation over time with a regular human insulin release profile following injection in a patient. In another embodiment, the formulation is designed to release insulin into systemic circulation over time with a prandial release profile following injection in a patient.

In some embodiments, the insulin formulation is administered to patients who are not fully insulin dependent. The formulation provides a sufficient amount of insulin to the patient during the day so that the patient does not require additional insulin-containing formulations to maintain his/her blood glucose levels within a safe range. The patient is typically not fully insulin dependent.

In another embodiment, the formulation is administered to a patient who is receiving intensive insulin therapy as one of the insulin-containing formulations administered to the patient during the day. Preferably the formulation delivers insulin to the patient with a basal release profile.

The present invention will be further understood by reference to the following non-limiting examples.

EXAMPLES

Materials and Instrumentation

All chemicals were purchased from Sigma-Aldrich unless otherwise specified, and were used as received.

Human recombinant insulin (Zn salt, 27.5 IU/mg) was purchased from Invitrogen.

Deionized water was prepared by a Millipore NanoPure purification system (resistivity higher than 18.2 $M\Omega \cdot cm^{-1}$).

Absorbance of assays was measured on a Thermo Scientific GENESYS 20 spectrometer.

Transmission electron microscopy (SEM) images of microgels were obtained on a JEOL 6320FV Field-Emission High-resolution SEM instrument.

Transmission electron microscopy (TEM) image of enzyme nanocapsules was obtained on a JEOL 200CX General Purpose TEM.

Zeta potential and particle size distribution were measured on the 90Plus Particle Size Analyzer by Brookhaven Instruments.

Laser scanning confocal microscopy images and fluorescence microscopy images of microgels were obtained with the Carl Zeiss LSM 700 Laser Scanning Microscope and the Zeiss Axiovert, respectively.

Far-UV circular dichroism (CD) spectra of insulin and released insulin from microgels were performed at 20° C. in a buffer containing 100 mM KH2PO4/K2HPO4, pH 7.4 (Aviv Model 202 Circular Dichroism Spectrometer).

Solution pH was measured by the Mettler Toledo pH meter.

Statistical Analysis Student's t-test or ANOVA were utilized to determine statistical significance between different groups. A p value<0.05 was considered to be statistically significant.

Example 1

Preparation and Characterization of Enzyme Nanocapsules

Materials and Methods

A volume of 12 mg GOx or CAT in 4.0 mL of pH 8.5, 50 mM sodium carbonate buffer was reacted with 6 mg N-acryloxysuccinimide in 40 µL dimethyl sulfoxide (DMSO) for 2 h at room temperature.

Buffer exchange with 1×PBS was carried out for three times (Amicon Ultra-15 50 K devices, Millipore Corp.). The degree of modification was 23 vinyl groups per GOx or 32 vinyl groups per CAT, measured using 2,4,6-Trinitrobenzene Sulfonic Acid (TNBSA, Thermo Fisher Scientific Inc.).

Modified enzyme (e.g., functionalized with polymerizable groups, such as vinyl groups) was diluted to 1 mg/mL with 10 mM pH 8.5 sodium bicarbonate buffer. 40 μL acrylamide (AAm) monomer, prepared in a 200 mg/mL aqueous solution, was added to 6 mL of protein solution with stirring for 10 min at 4° C. The other monomer N-(3-Aminopropyl)methacrylamide (APMAAm) was added. Afterwards, crosslinker N,N'-methylene bisacrylamide was added. The molar ratio of AAm/APMAAm/crosslinker was adjusted to 8/4/1.

The polymerization was initiated by adding 4 mg of ammonium persulfate (APS) dissolved in 40 μL of deoxygenated and deionized water and 4 μL of N,N,N',N'-tetramethylethylenediamine (TEMED). The polymerization was allowed to proceed for 90 min in a nitrogen atmosphere at room temperature.

Buffer exchange with 1×PBS was performed to remove unreacted monomers and initiators. The yield of the enzyme nanocapsules was higher than 95%. The unmodified enzymes were removed using size-exclusion chromatography.

Results

Figures 2A, 2B:
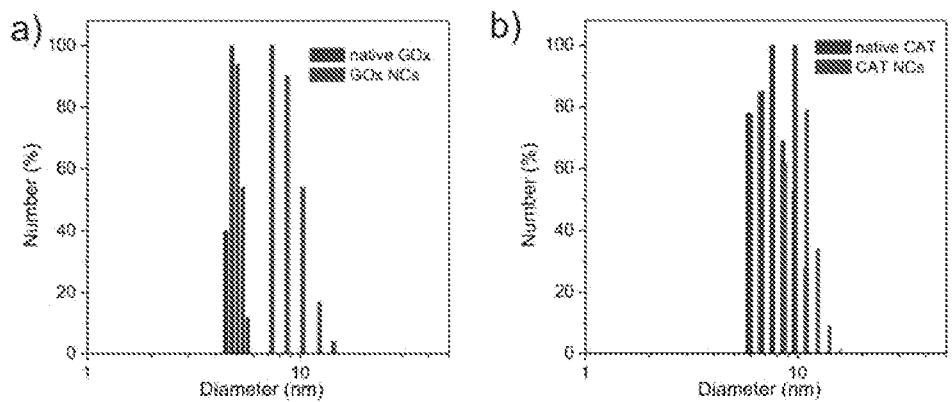
FIG. 2A is a bar graph showing the hydrodynamic sizes of native glucose oxidase (GOx) (dark colored bars) and GOx encapsulated in nanocapsules (light colored bars) as measured by dynamic light scattering (DLA).
FIG. 2B is a bar graph showing the hydrodynamic sizes of native catalase (CAT) (dark colored bars) and CAT encapsulated in nanocapsules (light colored bars) as measured by dynamic light scattering (DLA).

Enzyme nanocapsules were spherical and uniform in size, with a diameter of ~12 nm as determined by the transmission electron microscopy (TEM) and dynamic light scattering (DLS) analysis (FIGS. 2A and 2B).

The protein content in nanocapsules was determined by the bicinchoninic acid (BCA) colorimetric protein assay. Briefly, a tertrate buffer (pH 11.25) containing 25 mM BCA, 3.2 mM CuSO4, and appropriately diluted protein/NCs was incubated at 60° C. for 30 min. After the solution was cooled to room temperature, absorbance readings at 562 nm were determined with a UV-Vis spectrometer (Thermo Scientific GENESYS 20). BSA solutions with known concentrations were used as standards.

Figures 3A, 3B:
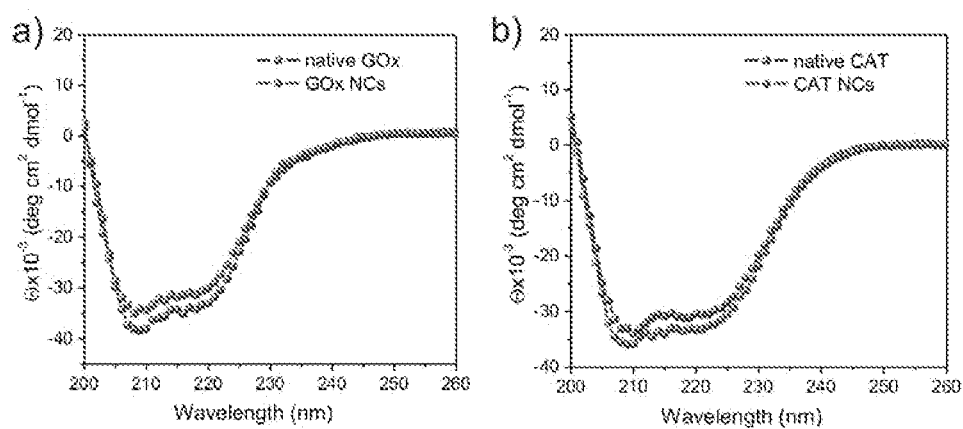
FIG. 3A is a circular dichroism (CD) spectrum of native GOx and GOx encapsulated in a nanocapsule.
FIG. 3B is a circular dichroism (CD) spectrum of native CAT and CAT encapsulated in a nanocapsule.

The Circular Dichroism (CD) spectra of the native and the enzyme nanocapsules confirmed that the enzymes retained the secondary structure of native proteins. The results are shown in FIGS. 3A and 3B.

Figures 4A, 4B, 4C:
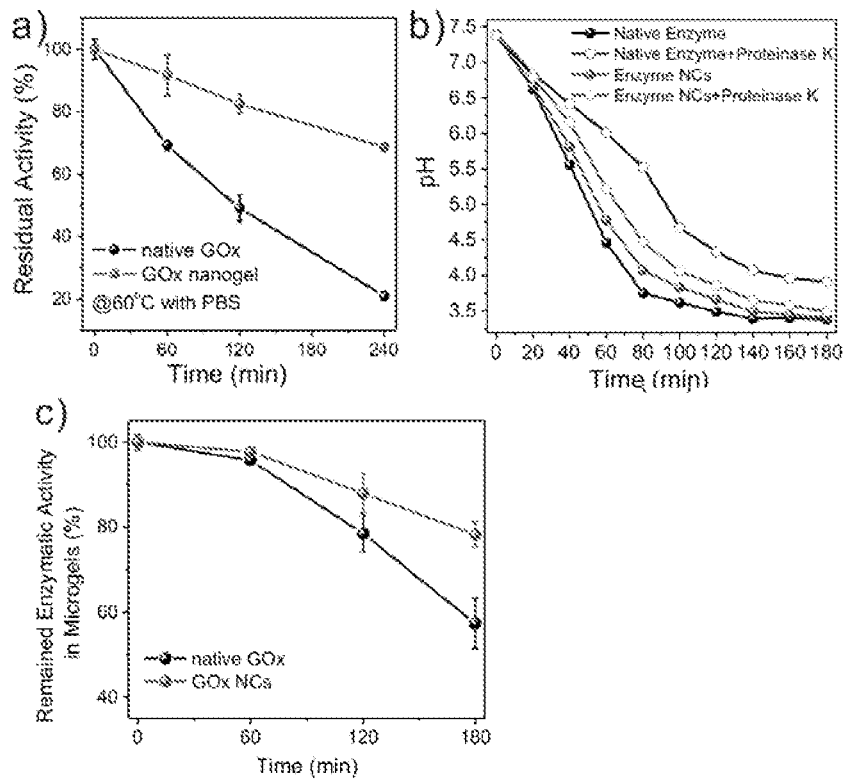
FIG. 4A is a graph showing enzyme stability (% residual activity) of native GOx (bottom curve) and GOx nanogels (top curve) as a function of time (minutes) at 60° C. in PBS buffer.
FIG. 4B is a graph comparing catalytic activity of native enzymes (mixture of GOx and CAT, 0.15 mg/mL, weight ratio of GOx to CAT:4:1) and enzyme nanocapsules incubated with a 400 mg/dL glucose saline solution after incubation with proteinase K (1 mg/mL) at 37° C. for 24 hours.
FIG. 4C is a graph showing remained enzymatic activity of native GOx and GOx nanocapsules in microgels (without CAT or CAT nanocapsules) incubated with a 400 mg/dL glucose saline solution, quantified over time by the Amplex® Red Glucose/Glucose Oxidase Assay Kit.

The enzymatic activity of native GOx and GOx nanocapsules was tested by the Amplex® Red Glucose/Glucose Oxidase Assay Kit (Invitrogen). Thermal stability of the native and the GOx nanocapsules was compared by incubating at 60° C. After 4 hours, the enzyme nanocapsule retained 70% of its original activity, whereas the native GOx retained only 20% of its original activity, as shown in FIG. 4A. The enhanced thermal stability of the enzyme nanocapsules is likely due to covalent attachment to the protective polymer. Remaining enzyme activity of the enzyme in native GOx and GOx nanocapsules after encapsulation in microgels incubated with a 400 mg/dL glucose saline solution is shown in FIG. 4C. After 3 hours, the GOx nanocapsules retained roughly 80% activity compared to about 60% for native GOx.

Figure 5:
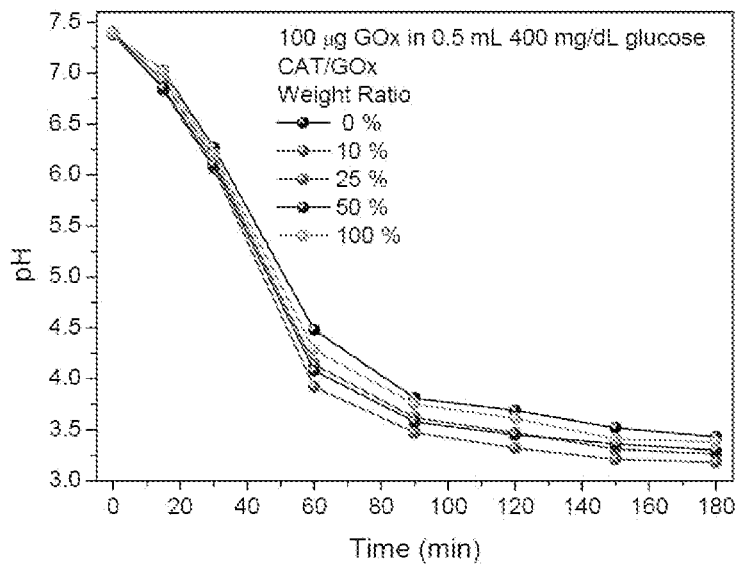
FIG. 5 is a graph showing the pH decrease in 0.5 mL 400 mg/dL glucose saline solution at 37° C. over time in the presence of GOx and CAT with different weight ratios.

To further validate the protective properties of the nanocapsules, enzyme nanocapsules and native enzymes were incubated in 1×PBS solution with proteinase K, which degrades exposed proteins. After 24 hours at 37° C., samples were exposed to 400 mg/dL glucose solution (a typical hyperglycemic level) to determine the enzymatic activity of GOx. As shown in FIG. 4B, the rate of pH decrease with native enzymes was reduced after incubation with proteinase K. In contrast, the rate of pH decrease with enzyme nanocapsules was only slightly reduced. Collectively, it can be inferred that the polymeric shell around the enzymes enhances their stability and protect from loss in activity. Since a higher concentration of CAT would result in less accessible sites on GOx and thus hinder enzymatic oxidation of glucose, the weight ratio of GOx to CAT was optimized and maintained at 4:1 (see FIG. 5).

Example 2

Preparation and Characterization of Insulin Releasing Microgels

Materials and Methods

Using chitosan as a model polymer, a closed-loop based smart insulin delivery system endowed with islet-cells-like function was prepared. Chitosan was selected because it is biocompatible, readily protonated in vivo (pKa: 6.2-6.8), and inexpensive.

Figure 6:
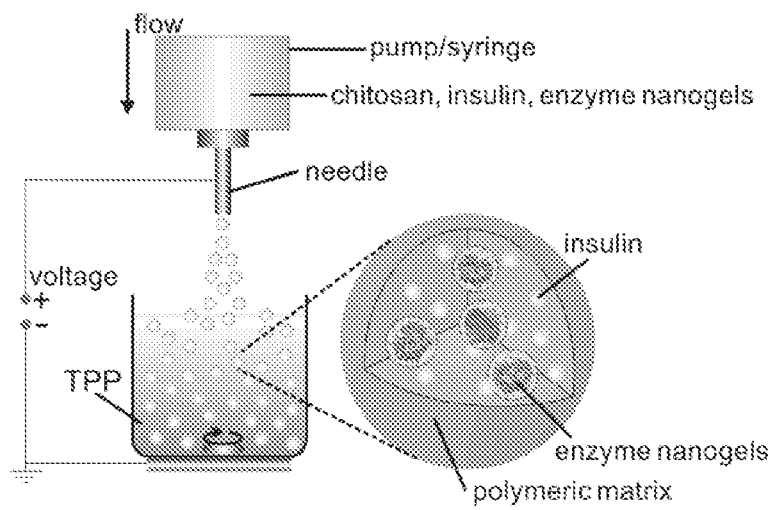
FIG. 6 is a schematic of fabrication of glucose-responsive insulin encapsulated microgels through electrospraying.

To prepare chitosan-based microparticles, a high-voltage electrospraying system based one-step process was utilized to obtain narrow size-distributed particles. Tripolyphosphate (TPP), a non-toxic biocompatible crosslinker, was used to crosslink chitosan matrix encapsulated with enzyme nanocapsules and insulin through ionic interactions between positively charged amino groups and negatively charged counterions of TPP. A schematic diagram of the experimental equipment is shown in FIG. 6.

An aqueous solution of chitosan (2% w/v) was prepared by dissolving sterilized chitosan powder (molecular weight: ~200 kDa, degree of acetylation 75%) in 1% acetic acid solution. The solution obtained was centrifuged at 10000 rpm to remove undissolved impurities.

Insulin and enzyme nanogels (as prepared above) were added and thoroughly mixed with the chitosan solution. The weight ratio of chitosan/insulin/enzymes was 40/30/3.75 or 50/50/4.8.

The homogeneous mixture was transferred into a 5 mL syringe with an attached blunt tip, 30 gauge metal needle. The syringe was placed in an electrospray system equipped with a syringe pump. The positive electrode of the electrospray system was connected to the needle and the negative electrode was connected to a metal receiving container with 50 mL 5% TPP (pH=9.4). The solution was sprayed at high voltage (9 kV) to the receiving container with gentle agitation (FIG. 6). The collected particles were washed with 1× Phosphate buffered saline (PBS) twice and concentrated by centrifugation at 2000 rpm.

Results

The microgels were stored at 4° C. with a final density of 2000 particles/mL (insulin content:~3.2 mg/mL).

Figure 7:
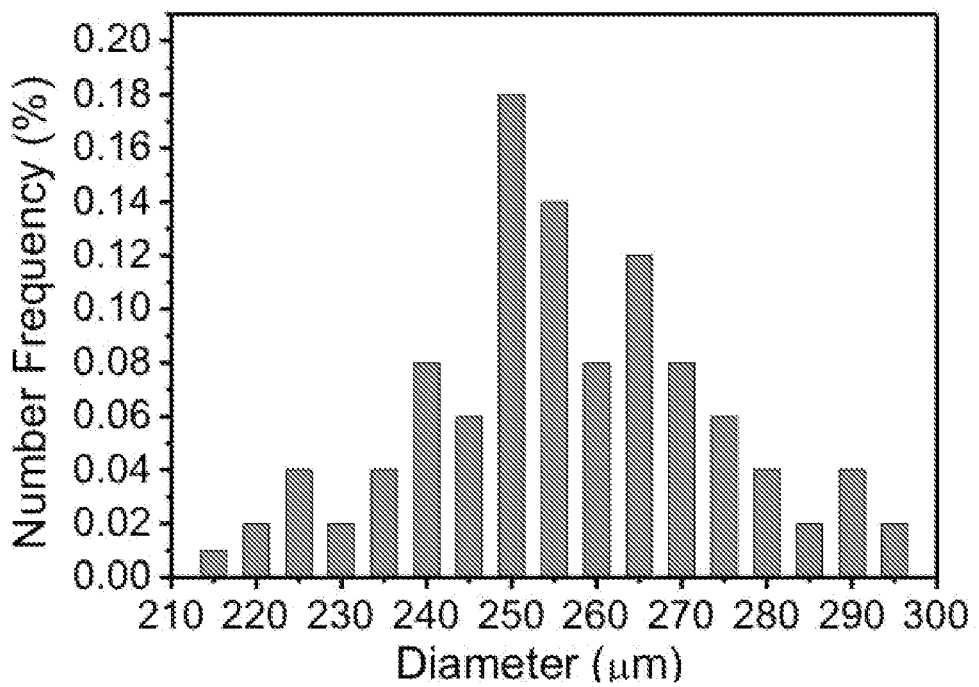
FIG. 7 is a bar graph showing the diameter distribution of insulin encapsulated microgels made according to the method diagrammed in FIG. 6.

In order to prepare microgels of uniform size, the applied voltage and the flow rate of the electrospray were adjusted to achieve optimal conditions. Using 250 μL/min as a flow rate, spherical and monodispersed gel particles with a diameter of 256±18 μm were obtained (FIG. 7).

The loading capacity (LC) and encapsulation efficiency (EE) of the microgels were calculated as:

$$LC=(A-B)/C, EE=(A-B)/A,$$

where A was the expected encapsulated amount of insulin or enzyme, B was the free amount of insulin or enzyme in the collection solution and C was the total weight of particles. The results are shown in Table 1.

TABLE 1

Insulin/enzymes loading capacity (LC) and encapsulation efficiency (EE) of microgels

|        | MGs (E + I)* | MGs (I)    | MGs (E)**  |
|--------|--------------|------------|------------|
| LC (%) | 44.6 ± 2.8   | 46.1 ± 3.5 | 54.3 ± 1.6 |
| EE (%) | 59.7 ± 3.4   | 58.9 ± 2.0 | 67.2 ± 2.6 |

*insulin based LC and EE, calibrated using microgels encapsulated with enzyme nanocapsules only;
**GOx based LC and EE.

An optimal insulin loading capacity (LC) of 44.6±2.8% and encapsulation efficiency (EE) of 59.7±3.4% was obtained. Scanning electron microscope (SEM) images revealed the porous structure of particles after lyophilization.

Laser scanning confocal microscopy (LSCM) images verified that encapsulated fluorescent dye-stained insulin and nanocapsules were homogeneously distributed inside microgels. The confocal images indicate that insulin is stably encapsulated within matrix of particles with negligible diffusion, as there was a clear demarcation between the microparticles and the background. This observation can be attributed to the strong electrostatic and van der Waals interactions between insulin and chitosan chains.

Example 3

In Vitro Insulin Release in a Glucose-Responsive Fashion

Materials and Methods

To determine glucose response capability of the microgels, microgels (insulin content: ~0.25 mg) were collected by spinning down to pellets at 3000 rpms for 30 seconds and incubated with 0.5 mL 1×PBS solutions with different glucose levels: hyperglycemic level (400 mg/dL), normal level (100 mg/dL) and control level (0 mg/dL) glucose solution in a 48-well plate, which was left on a heating stage fixed at 37° C.

Optical or fluorescence microscopy images of microgels incubated in different solutions were separately recorded over time. For plotting accumulated release profile, microgels were similarly incubated with solutions at different glucose levels at 37° C. At predetermined time points, the sample was gently shaken for 30 seconds and 12 µL of the supernatant was removed for analysis. 12 µL of fresh solution was then added to the tube to maintain a constant volume and placed back within the incubator.

Total insulin content was measured using a Coomassie Plus Protein Assay. The absorbance of the well was detected at 595 nm and the concentration was interpolated from an insulin standard curve and a calibration curve made using microgels encapsulated with enzyme nanocapsules only.

To assess the self-regulated release profile, microgels were first incubated in 100 mg dL-1 glucose for 1.5 hours at 37° C. The sample was then centrifuged at 3000 rpm for 30 seconds and all of the supernatant was recovered.

Next, the sample was incubated in 400 mg dL-1 glucose for another 1.5 hours. This cycle was repeated for subsequent alternated cycles. Similarly, insulin concentration was determined using the Coomassie Plus Protein Assay.

The insulin release rates were determined by the slope of the curves. Bioactivity of released insulin from microgels was tested by the stimulation of insulin receptor based AKT phosphorylation assay.

CHO-M1 cells (ATCC) were seeded at 25,000 cells/well in a 96 well plate and allowed to grow for 24 hours before serum-starving overnight. Serum-starved cells were treated with insulin samples with different concentrations for 10 minutes. Cells were then lysed and AKT phosphorylation at 5473 was assayed according to manufacturer's protocol (AlphaScreen, Perkin Elmer).

Results

Figure 8A:
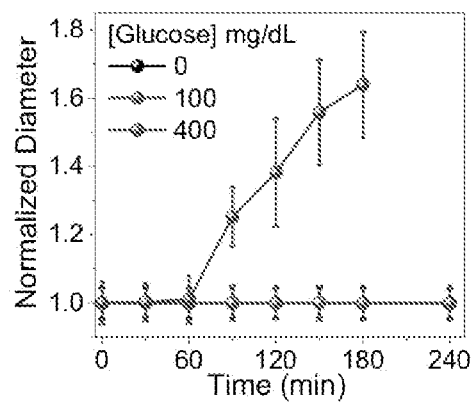
FIG. 8A shows normalized microgel particle diameter changes as a function of time.

As shown in FIG. 8A, microgels treated with solution at the hyperglycemic glucose levels steadily swelled over time. Within 3 h, the particles exhibited an approximately 1.7-fold change in diameter, corresponding to an approximately 5 fold volume change. The catalysis of glucose to gluconic acid through enzyme nanogels resulted in a decrease of solution pH from 7.4 to 6.6 (FIG. 8B), suggesting the protonation of primary amines of chitosan leads to the swelling response of microgels. After 4 hours, the microgels were fully dissociated and the solution became transparent (FIG. 8A). In contrast, similar to the control sample, microgels treated with normal glucose level did not display perceptible swelling within 4 h, which associated with a slight decrease of solution pH.

Figure 8B:
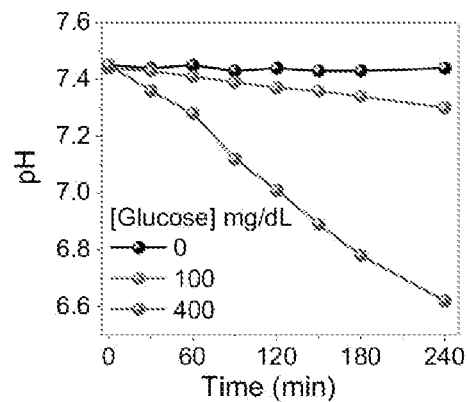
FIG. 8B shows pH changes following incubation with different glucose concentrations.
Figure 8C:
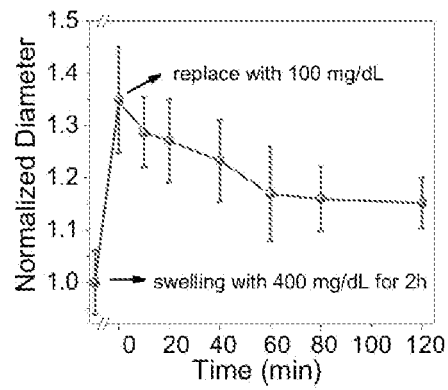
FIG. 8C shows normalized microgel particle diameter changes following initial incubation with 400 mg/mL glucose and subsequent incubation with 100 mg/dL glucose.

Microgels were also first incubated with 400 mg/dL glucose for 2 hours, then the solution was replaced with 100 m mg/dL for 2 hours. As shown in FIG. 8C, swollen microgels steadily shrank over time. It is hypothesized that deswelling of microgels was driven by the dissociation of hydrogen ion from the chitosan when exposed to a neutral pH solution. Microgels cannot completely revert to the original state, in part due to disassembly of some of the polymeric chains and polyanions into the solution during the swelling process. The diameter of the particles was measured to determine deswelling in response to normalizing concentrations of glucose.

Figures 9A, 9B:
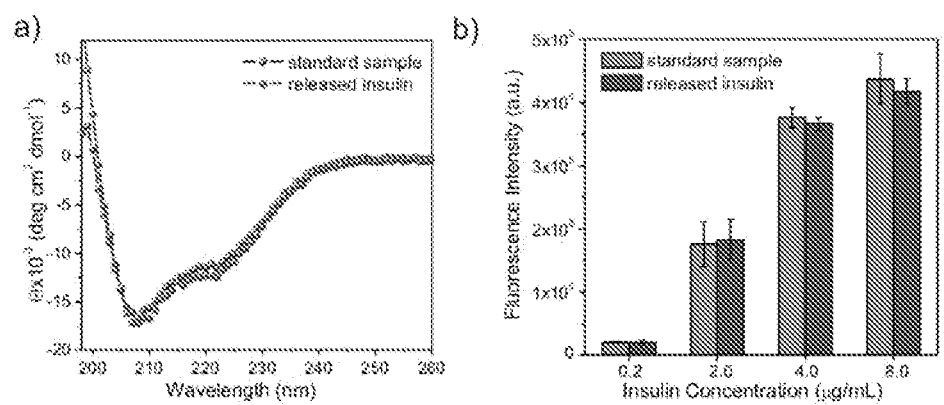
FIG. 9A is CD spectra of standard insulin solution and insulin released from microgels.
FIG. 9B is a bar graph showing insulin activity assays on serial dilutions of standard insulin and insulin released from microgels by AKT phosphorylation following stimulation of the insulin receptor.

To demonstrate temporal release of insulin from the microgel, microgels encapsulating FITC-conjugated insulin were incubated in 400 mg/dL glucose solution at 37° C. for 150 min. Fluorescence images of microgels were recorded and analyzed over time. As the microgel sizes increased, the fluorescence intensity of the microgel gradually decreased, and the fluorescence intensity of solution increased, indicating that the encapsulated insulin steadily released from chitosan matrix into the exterior solution. Furthermore, the CD spectrum of the released insulin from microgels matched that of free insulin (FIG. 9A).

To confirm the bioactivity of the released insulin, the activity of insulin released from microgels was evaluated using a cell-based assay that quantifies AKT phosphorylation, which follows the stimulation of insulin receptor by a native insulin. Released insulin retained bioactivity comparable to standard samples at the same of concentrations (FIG. 9B). The enzymatic activity of GOx nanocapsules was maintained in the microgel matrix during expansion when compared with native GOx (FIGS. 4A-4C)

The accumulated insulin release plot determined by the Bradford protein assay validated that microgels can continuously release insulin in response to the hyperglycemic glucose level. Briefly, insulin release profiles were studied as follow: after incubation of microgels in a certain glucose solution (400 mg/dL glucose or 100 mg/dL glucose) in a 48 well-plate for 1.5 hours, the glucose solution was carefully transferred away by a pipette and gently replaced with fresh glucose solution (100 mg/dL glucose or 400 mg/dL glucose) using a pipette for following incubation.

Figure 10A:
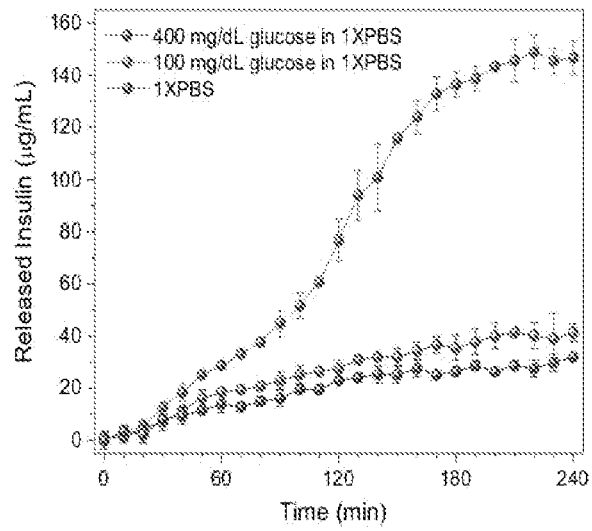
FIG. 10A shows in vitro accumulated release of insulin at different glucose concentrations in 1×PBS solution.
Figure 10B:
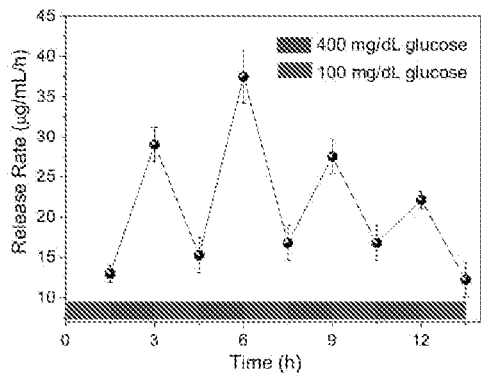
FIG. 10B shows the self-regulated profile of microgels presented as a function of glucose concentration. Data points represent mean+/−SD (n=3).

Microgels substantially released insulin at hyperglycemic glucose levels (FIG. 10A). In contrast, a much slower release rate was obtained when the microgels were exposed to the basal glucose level and control solutions. These results are consistent with the observed swelling response (FIGS. 8A and 8B). Importantly, the insulin release profile of microgels presents a pulsatile pattern exposed to an alternating glucose concentration between normal and hyperglycemic levels every 1.5 hours for several cycles. Microgels responded to changes in glucose levels with a 2.5-fold increase in the insulin release rate when the glucose concentrations were elevated to hyperglycemic levels (FIG. 10B). Interestingly, the release rates at high hyperglycemic level reached a maximum point and then gradually decreased. The "acceleration period" was a result of the incomplete reversibility between swelling and deswelling, while the "deceleration period" was due to the depletion of insulin in the dissociated microgels. In addition, the profile exhibits a basal release rate at normal glucose levels, which is obviously lower than that at hyperglycemic levels.

Example 4

In Vivo Studies Using STZ-Induced Diabetic Mice

Materials and Methods

The efficacy of the insulin-loaded microgels for diabetes treatment was evaluated in vivo using Type 1 diabetes, streptozotocin (STZ)-induced adult diabetic mice (male C57B6, Jackson Lab, USA). Mice were cared for under supervision of MIT's Division of Comparative Medicine and in compliance with NIT's *Principles of Laboratory Animal Care*.

The blood glucose levels of mice were continuously tested for two days before administration by collecting blood (~3 µL) from the tail vein and measuring using the Clarity GL2Plus Glucose Monitor (VWR, USA). 250 µL of microgel solutions or PBS solution was injected using a 1 cc syringe with a 19-gauge needle into the subcutaneous dorsum of mice (insulin dose: 40 mg/kg) that had been anesthetized with 1% isoflurane. The glucose level of each mouse was monitored over time. To measure in vivo insulin concentration, blood samples (~25 µL) were drawn from the tail vein of mice and collected into Sarstedt serum gel microtubes. Serum samples (5 µL) were stored frozen at −20° C. until assayed. Plasma insulin concentrations were determined using the human insulin ELISA kit (Calbiotech, USA).

The mice were divided into four groups and subcutaneously injected with microgels containing human recombinant insulin with enzyme nanocapsules (MGs(I+E), 6 mice), microgels encapsulated with insulin only (MGs(I), 6 mice) or enzyme nanocapsules only (MGs(E), 6 mice), and control (1×PBS, 6 mice) solution. The blood glucose levels (BGLs) of each animal group were closely monitored after administration and continuously recorded for 6 days.

Results

Figures 11A, 11B, 11C:
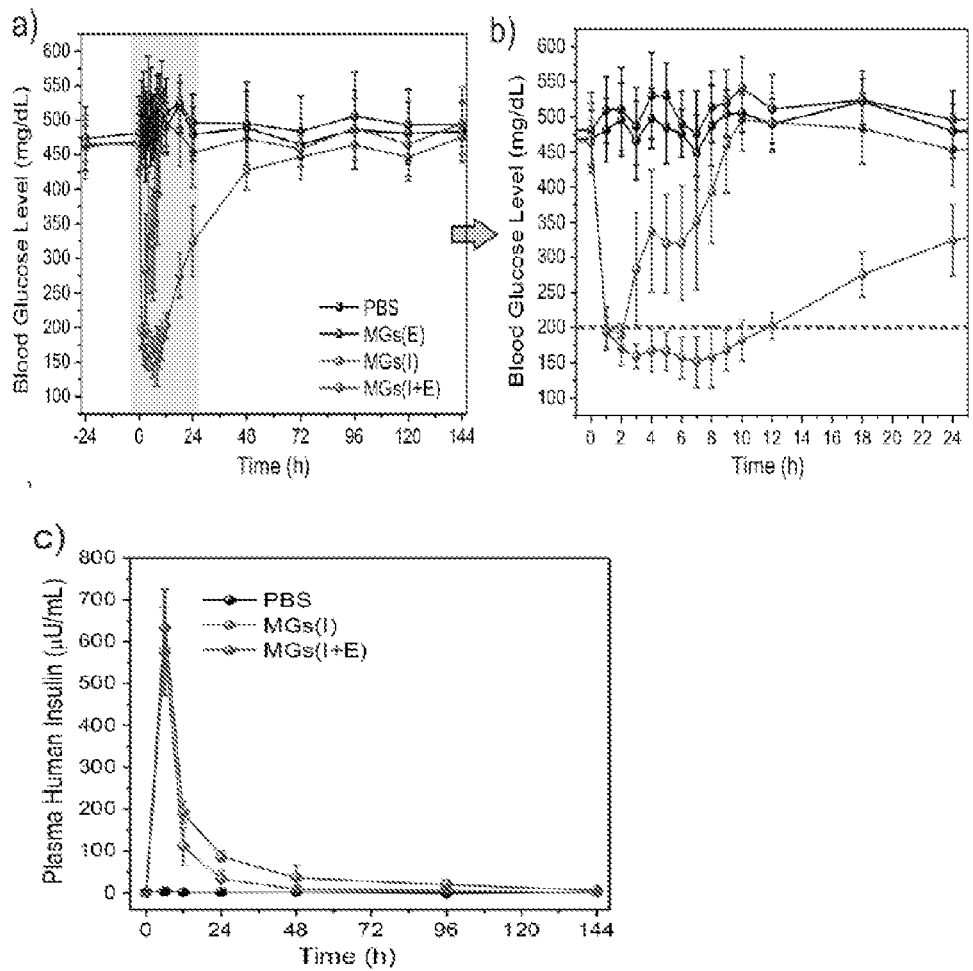
FIG. 11A is a graph showing blood glucose levels in STZ-induced C57B6 diabetic mice after subcutaneous injection with 1×PBS, microgels encapsulated with insulin and enzymes (MGs(E+I)), microgels encapsulated with insulin only (MGs(I)), microgels encapsulated with enzymes only (MGs(E)).
FIG. 11B is a graph showing blood glucose levels of each animal group within 24 hours after administration, extracted from the shaded part of (a).
FIG. 11C is a graph showing plasma human insulin levels of mice treated with 1×PBS, MGs(E+I) and MGs(I) over the administration time.

As shown in FIGS. 11A and 11B, BGLs of mice injected with MGs(I+E) or MGs(I) (insulin dose: 40 mg/kg) quickly declined to a normoglycemic state (<200 mg/dL) within 2 hours. This was attributed to an initial burst release of dissolved insulin in the injection solution and adsorbed insulin on the surface of microgels. The BGLs of mice with MGs(I+E) were then maintained in the normoglycemic range for up to 12 hours and gradually increased afterwards.

In absence of the enzyme nanocapsules, the BGLs of mice with MGs(I) steadily increased back to a hyperglycemic state 2 hours after injection. Correspondingly, mice treated with MGs(I+E) presented a consistently higher plasma insulin level (PIL) for at least 96 hours than those treated with MGs (I), as quantified by ELISA (FIG. 11C). Moreover, similar to the PBS control group, the group treated with MGs(E) did not display noticeable decline in BGLs, suggesting the catalytic conversion of glucose did not considerably affect BGLs.

Example 5

Biocompatibility Analysis

Materials and Methods

Cytotoxicity study toward microgels was performed using HeLa cells. Cells were seeded into 96-well plates at a density of 5,000 cells per well and cultivated in 100 µL of Dulbecco's Modified Eagle Medium (DMEM) with 10% bovine growth serum (BGS). The plates were then incubated in 5% $CO_2$ and at 37° C. for 12 h to reach 70-80% confluency before addition of serial dilutions of the empty microgels.

Figure 12:
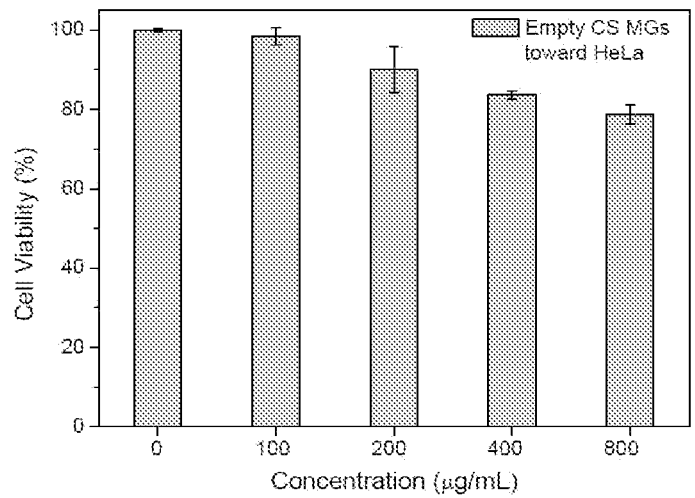
FIG. 12 is a bar graph showing the cytotoxicity study of empty chitosan microgels after culture with HeLa cells for 24 hours.

After incubation with microgels for 24 hours, the cells were washed with PBS solution and incubated with 100 µL fresh DMEM and 20 µL MTS solution (CellTiter 96® AQueous One Solution Cell Proliferation Assay, Invitrogen). The plates were incubated for an additional 3 h. The absorbance of the plates was read at 550 nm and a reference wavelength of 690 nm using a microplate reader (PowerWave X, Bio-tek Instruments, USA). The results are shown in FIG. 12.

Microgels were retrieved from mice 3 days after administration to assess toxicity. To evaluate the biocompatibility of microgels, mice were euthanized via $CO_2$ asphyxiation and the injected materials and surrounding tissues were excised. The tissues were then fixed in 10% formalin, embedded in paraffin, cut into 5 µm sections, and stained using hematoxylin and eosin (H&E) for histological analysis.

Results

Figure 13:
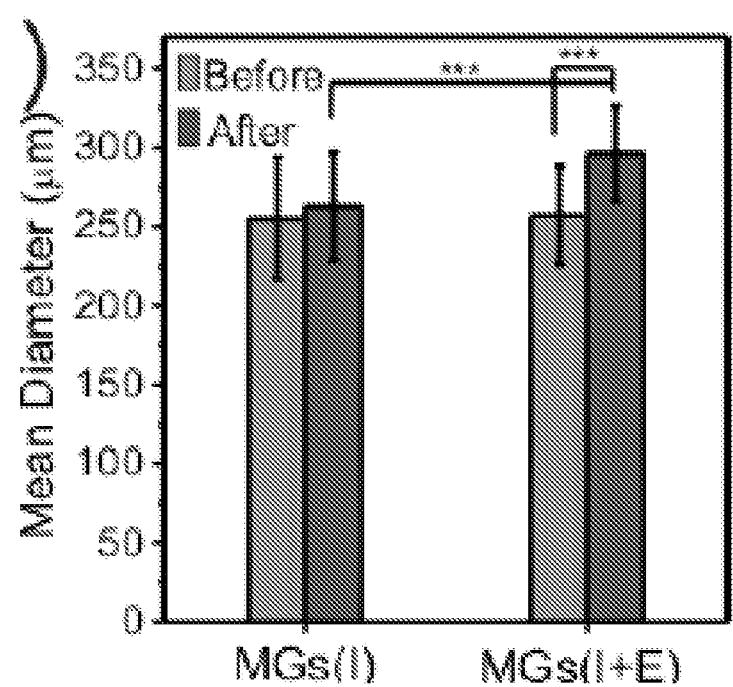
FIG. 13 is a bar graph showing changes of mean diameters of MGs(E+I) and MGs(I) 3 days after administration. Data points represent mean±SD (n=50) and *** represents $p<0.001$ by the student's t-test.

Microgels with insulin only had a clear circular profile and can be distinguished individually. In contrast, particles containing enzymes were closely adhered to each other with a bulk gel-like morphology. Further histological investigation of tissue containing injected microgels after 3 days indicated that chitosan microgels induced acute inflammation. However, chitosan is used medically and is enzymatically degradable. The microgels completely degraded 4-6 weeks later and no fibrotic encapsulation was observed (FIG. 12). MGs(I+E) had a significant increase in the mean diameter after implantation, compared with MGs(I) (FIG. 13). This is consistent with swelling induced by enzymatic reactions as observed in vitro. This also explains the substantial release of insulin and prolonged maintenance of a normoglycemic state for the system associated with enzymes. Swelling is reduced when compared to the in vitro studies, presumably due to tissue restrictions or buffering in the body.

We claim:

1. A glucose-responsive injectable formulation for delivering insulin to a subject in need thereof, comprising pH-responsive polymeric microgels having
    (a) insulin entrapped in the microgels,
    (b) glucose oxidase entrapped in or bound to the microgels, and
    (c) an agent that reduces hydrogen peroxide, entrapped in or bound to the microgels,
    wherein the glucose oxidase, the agent that reduces hydrogen peroxide, or both are encapsulated in nanogels, which are then encapsulated within the microgels,
    wherein the polymeric microgels expand when pH decreases from physiological pH and shrink when pH increases towards physiological pH, thereby releasing insulin at a rate corresponding to the glucose concentration.

2. The formulation of claim 1, wherein the agent that reduces hydrogen peroxide is an enzyme selected from the group consisting of catalase and glutathione peroxidase, wherein the enzyme is encapsulated in polymeric nanogels.

3. The formulation of claim 1, wherein the pH-responsive polymeric microgels comprise a polymer selected from the group consisting of chitosan, polymethyacrylic acid (PAA), polymethyl methacrylate (PMMA), polyacrylamide (PAAm), polydimethylaminoethylmethacrylate (PDEAEMA) and polyethylene glycol, Tri polymer of N-vinyl-2-pyrrolidone methacrylamide and itaconic acid, polydimethylaminoethylmethacrylate, copolymer of poly methacrylic acid and polyethylene glycol, and a copolymer of cationic guar gum and acrylic acid monomer.

4. The formulation of claim 3, wherein the microgels are made from chitosan crosslinked with tripolyphosphate (TPP).

5. The formulation of claim 1 wherein the nanogels are made from biocompatible or biodegradable monomers or polymers.

6. The formulation of claim 1 wherein the insulin is selected from the group consisting of human insulin, recombinant human insulin, insulin from a non-human animal source, fast acting insulins, rapid-acting insulin analogs, intermediate-acting insulin, and long acting insulins.

7. A method of providing insulin to an individual in need thereof comprising injecting an effective amount of the formulation of claim 1 into the individual to maintain a normoglycemic state.

8. The method of claim 7 wherein the formulation is injected subcutaneously, intradermally or intramuscularly.

9. A method of making a glucose responsive insulin delivery system comprising forming pH-responsive polymeric microgels having
(a) insulin entrapped in the microgels,
(b) glucose oxidase entrapped in or bound to the microgels, and
(c) an agent that reduces hydrogen peroxide, entrapped in or bound to the microgels,
wherein the glucose oxidase, the agent that reduces hydrogen peroxide, or both are encapsulated in nanogels, which are then encapsulated within the microgels,
wherein the polymeric microgels expand when pH decreases from physiological pH and shrink when pH increases towards physiological pH, thereby releasing insulin at a rate corresponding to the glucose concentration.

10. The method of claim 9 wherein the glucose oxidase, the agent that reduces hydrogen peroxide, or both, are bound to the microgels.

11. The method of claim 8 wherein the insulin is co-encapsulated within the nanogels and microgels.

* * * * *